United States Patent [19]

Sackier et al.

[11] Patent Number: 5,496,333
[45] Date of Patent: Mar. 5, 1996

[54] LAPAROSCOPIC SURGICAL CLAMP

[75] Inventors: Jonathan M. Sackier, Del Mar; Michael L. Jones, Capistrano Beach; Edward E. Dolendo, Huntington Beach, all of Calif.

[73] Assignee: Applied Medical Resources Corporation, Laguna Hills, Calif.

[21] Appl. No.: 139,919

[22] Filed: Oct. 20, 1993

[51] Int. Cl.⁶ .................................. A61B 17/04
[52] U.S. Cl. ..................... 606/142; 606/151; 227/901; 227/902
[58] Field of Search ..................... 606/157, 158, 606/142, 143, 139, 151, 125; 24/500, 502, 503, 504, 515, 516, 523, 525, 526, 535, 536, 545; 227/901, 902

[56] References Cited

U.S. PATENT DOCUMENTS

| | | | |
|---|---|---|---|
| 3,032,849 | 5/1962 | Cohen et al. | 24/502 |
| 3,509,882 | 9/1967 | Blake . | |
| 3,510,923 | 6/1968 | Blake . | |
| 3,579,751 | 5/1971 | Jonckheere . | |
| 3,598,125 | 8/1971 | Cogley . | |
| 3,827,438 | 8/1974 | Kees . | |
| 3,882,854 | 5/1975 | Hulka et al. | 606/157 |
| 3,955,249 | 5/1976 | Shiozaki | 24/503 |
| 4,064,881 | 12/1977 | Meredith | 606/157 |
| 4,169,476 | 10/1979 | Hiltebrandt | 606/158 |
| 4,192,315 | 5/1980 | Hilzinger . | |
| 4,273,315 | 6/1981 | Kanamoto et al. . | |
| 4,340,061 | 7/1982 | Kees, Jr. et al. . | |
| 4,484,581 | 11/1984 | Martin et al. . | |
| 4,524,650 | 6/1985 | Marks | 81/57.39 |
| 4,658,822 | 4/1987 | Kees, Jr. . | |
| 4,660,558 | 4/1987 | Kees, Jr. . | |
| 4,671,282 | 6/1987 | Tretbar . | |
| 4,681,107 | 7/1987 | Kees, Jr. | 606/142 |
| 4,706,668 | 11/1987 | Backer | 606/142 |
| 4,739,838 | 4/1988 | Marks | 173/170 |
| 4,822,348 | 4/1989 | Casey | 606/157 |
| 4,869,268 | 9/1989 | Yoon . | |
| 4,971,055 | 11/1990 | von Zeppelin . | |
| 5,026,379 | 6/1991 | Yoon . | |
| 5,133,727 | 7/1992 | Bales . | |
| 5,133,735 | 7/1992 | Slater . | |
| 5,133,736 | 7/1992 | Bales, Jr. et al. . | |
| 5,141,519 | 8/1992 | Smith et al. . | |
| 5,147,373 | 8/1992 | Ferzli . | |
| 5,147,376 | 9/1992 | Pianetti . | |
| 5,152,778 | 10/1992 | Bales, Jr. et al. . | |
| 5,156,609 | 10/1992 | Nakao et al. | 606/143 |
| 5,156,633 | 10/1992 | Smith . | |
| 5,242,456 | 9/1993 | Nash et al. | 606/142 |
| 5,304,183 | 4/1994 | Gourlay et al. | 606/142 |
| 5,368,600 | 11/1994 | Failla et al. | 606/142 |

*Primary Examiner*—Gary Jackson
*Attorney, Agent, or Firm*—Richard L. Myers

[57] ABSTRACT

A surgical clamp combination includes a clamp movable between a free state and operable state, the clamp including a pair of jaws which can be operated to occlude a body conduit. A clamp applier is adapted to releasibly engage the clamp in the free state and to operate the clamp in the operable state to close the jaws. The applier has a housing disposed at a proximal end and a tube extending distally and configured to receive the clamp in the operable state. A shaft is disposed within the tube and movable between an extended position to engage the clamp in the free state and a retracted position to releasibly hold the clamp in the operable state. With the clamp in the operable state, the shaft is rotatable by operation of a handle and aladdin screw, to alternatively rotate in opposite directions to open and close the jaws of the clamp.

22 Claims, 5 Drawing Sheets

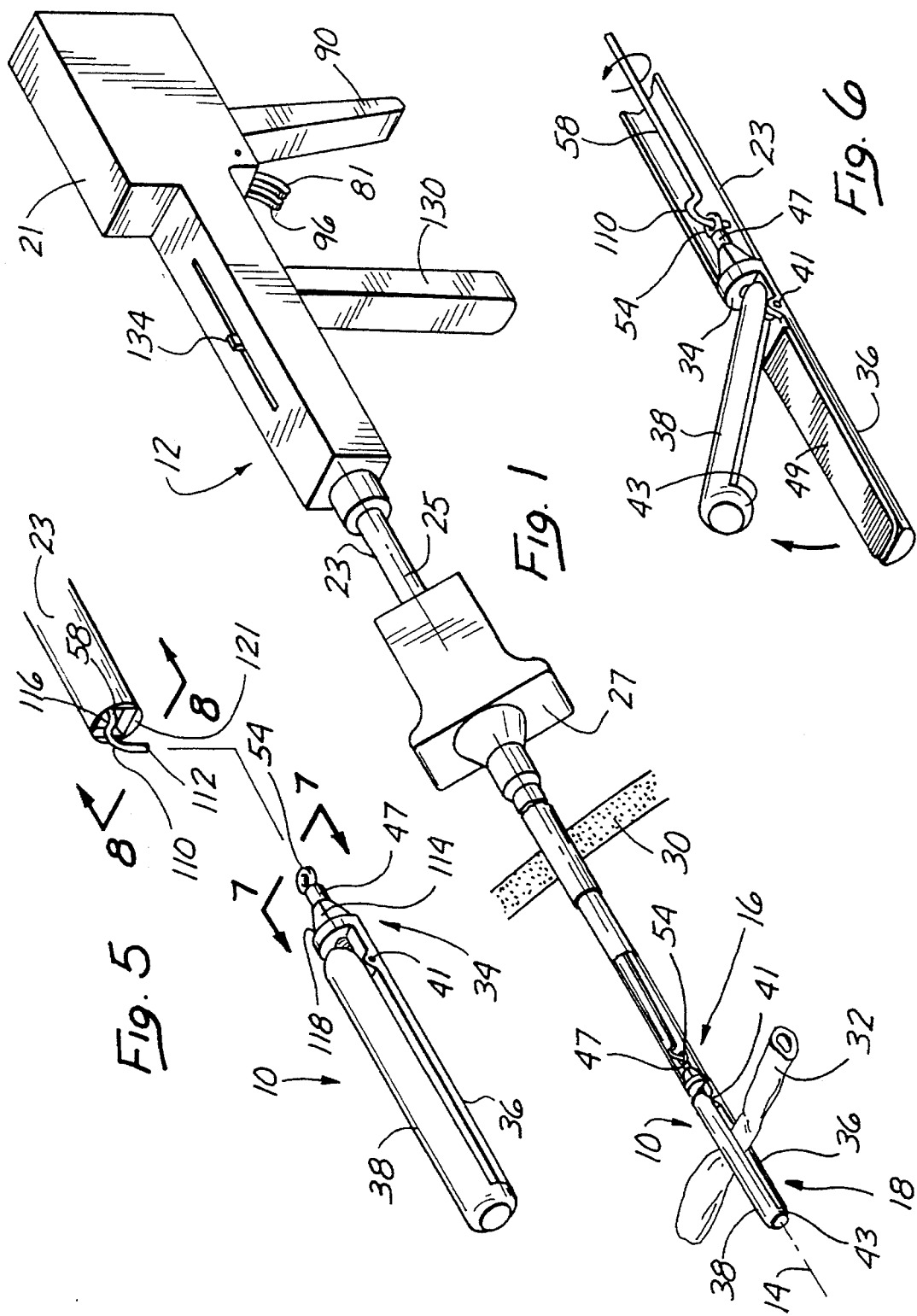

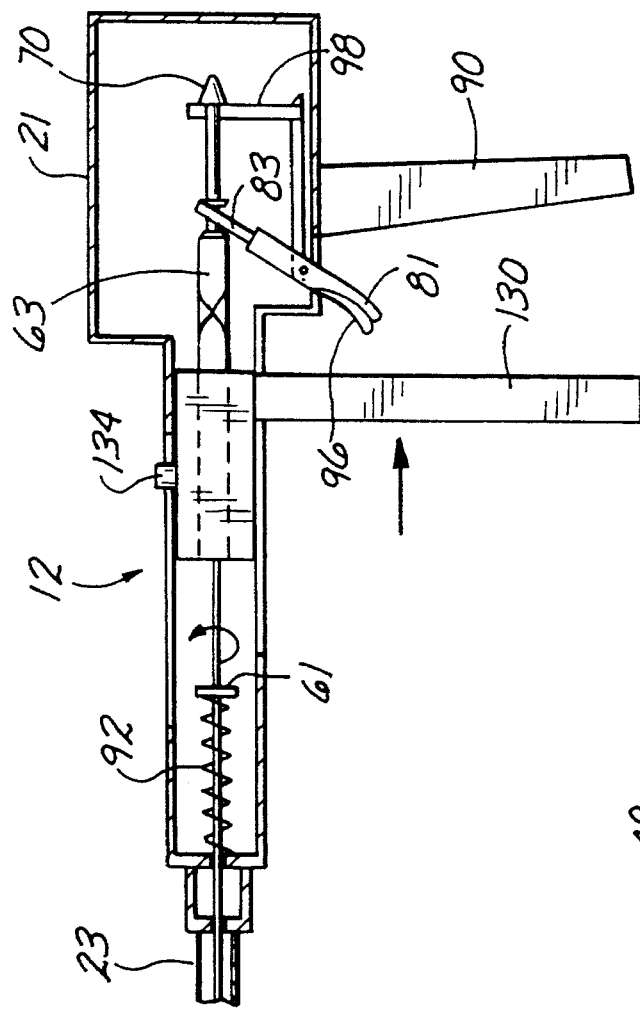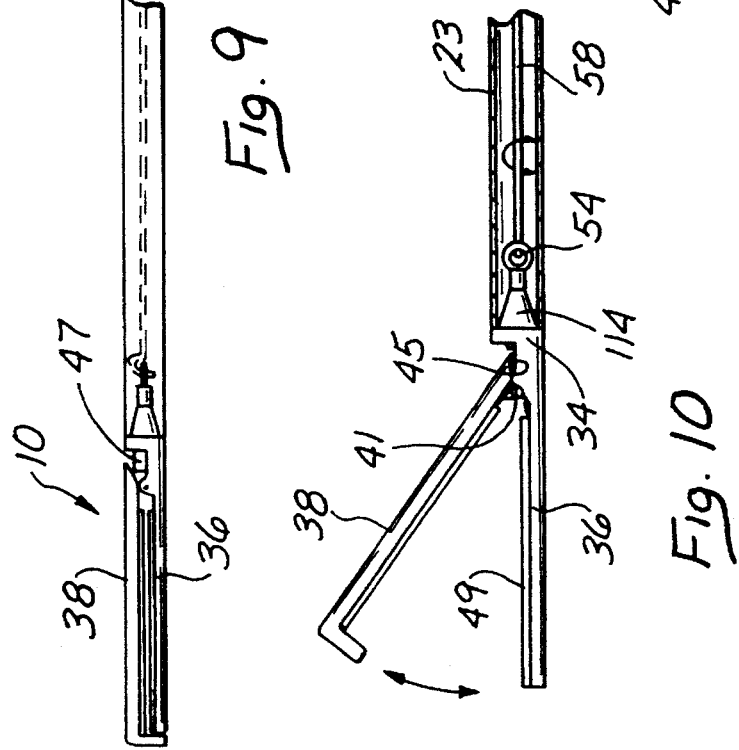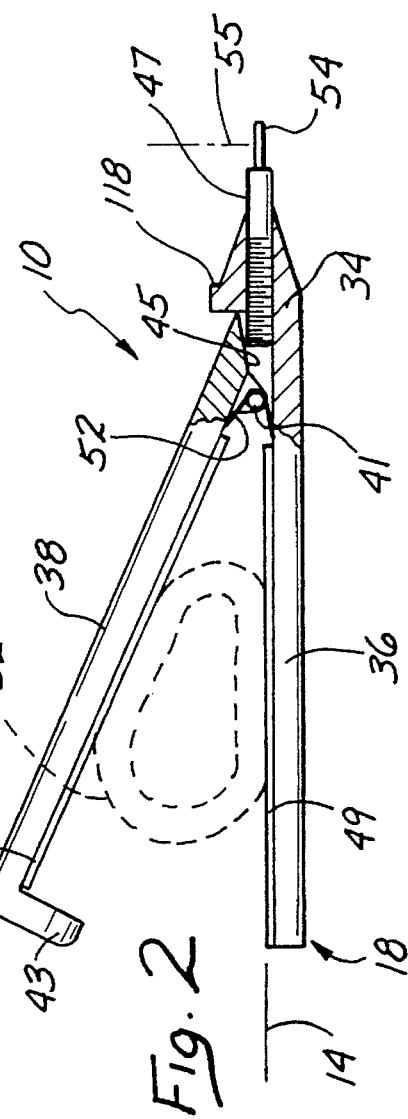

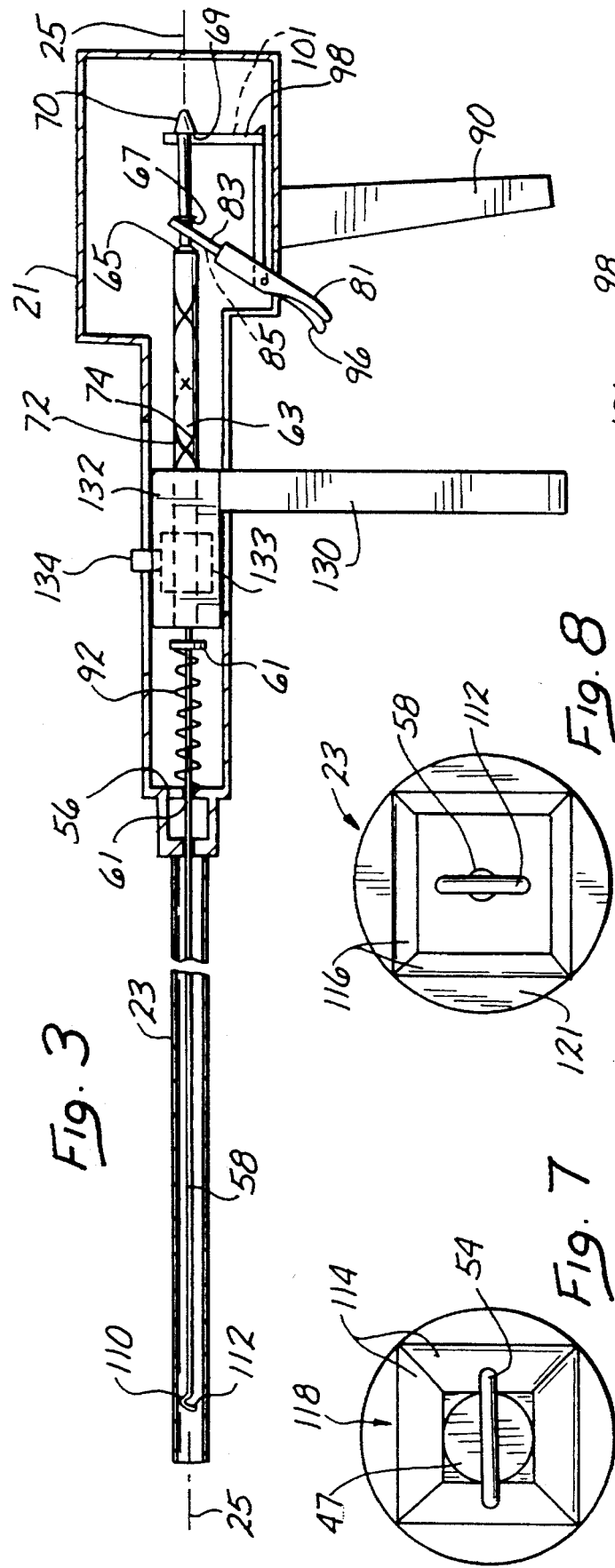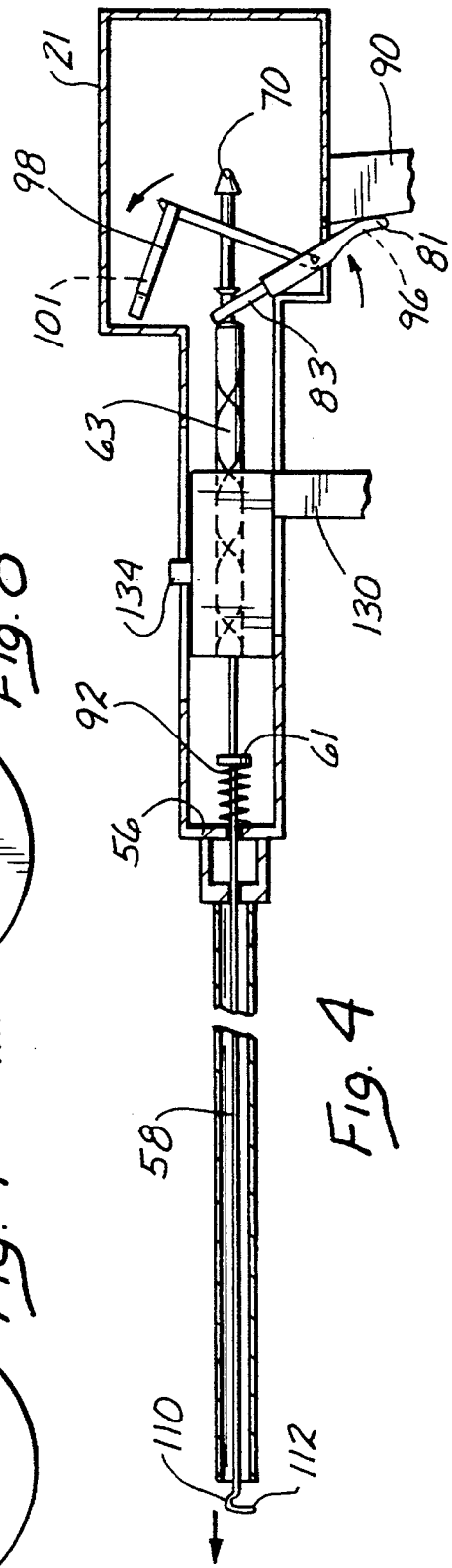

LAPAROSCOPIC SURGICAL CLAMP

BACKGROUND OF THE INVENTION

1. Field of the Invention

This invention relates generally to surgical clamp apparatus and more specifically to clamps and clamp appliers for use in occluding body conduits.

2. Discussion of the Prior Art

Alternatives to large incision, open surgery are becoming increasing important where they can provide reduced trauma and an increased speed of healing. For the patient, this ultimately equates to less time in the hospital which adds the economic advantage to these procedures.

Surgeries in the abdominal area are now being undertaken with a technique commonly referred to as laparoscopic surgery. In this procedure, access devices are used to puncture the abdominal wall or lapra and to provide working channels for instruments to perform the surgery. These access devices, commonly referred to as trocars, require relatively small incisions and provide working channels in a range of diameters between, for example, 5mm and 21mm.

Typical of these access devices is the trocar disclosed and claimed in applicant's patent U.S. Pat. No. 5,209,737 issued on May 11, 1993 which is incorporated herein by reference.

Since the objectives of the open surgeries and laparoscopic surgeries are often the same, it is not surprising that the occluding of body conduits is still of interest. However in the case of laparoscopic surgeries, this can be accomplished only with considerable difficulty due to the limited access provided by the trocars. Also, the confined abdominal cavity associated with laparoscopic surgeries generally requires additional retraction of organs in order to provide an enlarged surgical field.

Surgical clamps of the past have been adapted for open surgery wherein the size of the clamp is not constrained by the inside diameter of a trocar. These clamps commonly include long legs which form the jaws of the clamp and opposing smaller arms which are pivotal with the legs on a fulcrum disposed therebetween. These clamps are typically operable by a clamp applier which has a scissor configuration. The scissors of the applier in an open state engage the arms of the clamp and compress those arms to open the legs of the clamp. Unfortunately, with this configuration, either the long legs of the clamp are spread or the scissors are spread. In either case, this combination is not adapted for use with the narrow diameters offered by laparoscopic trocars.

The engagement mechanisms associated with these clamp systems of the prior art are also inappropriate for laparoscopic surgery. In the past, the clamp applier loosely engaged the clamp, this presented no problem to open surgery where one could merely reach into the cavity and retrieve a loose clamp. However, in laparoscopic surgery, the relatively closed surgical environment cannot tolerate this possibility of undesirable separation of the clamp from the applier.

SUMMARY OF THE INVENTION

These disadvantages of the prior art are overcome with the present invention which includes a novel surgical clamp and associated clamp applier both of which are insertable through a trocar. The clamp is provided with an elongate cylindrical configuration having an axis extending between the proximal end and a distal end. The clamp has two jaws which are relatively movable between an open state and a closed state. The first jaw may be formed as an extension of a supporting structure at the proximal end of the clamp, while the second jaw is pivotal on either the supporting structure or the first jaw. The second jaw is biased to an open state and includes a beveled surface which faces inwardly at the proximal end of the clamp. An axial screw is rotatable on the supporting structure and moves axially distally to contact the beveled surface. Further rotation of the screw performs a camming action with the beveled surface to close the second jaw against the first jaw. An annulus provided at the proximal end of the screw provides for positive engagement with the clamp applier.

The clamp applier includes a housing and an elongate tube which is sized and configured to move through the trocar. The clamp applier also includes an engagement mechanism having a hook which can be advanced to engage the annulus of the clamp. Retraction of the engagement mechanism moves the clamp into a rigid operative position on the applier. Biasing means and locking means cooperate to retain the clamp in the operative position. In this operative position the engagement mechanism can be rotated to open and close the jaws of the clamp.

A handle is provided on the housing and movable in a single direction. An aladdin screw is employed so that this single direction of movement can be converted into either clockwise or counterclockwise rotation of the engagement mechanism.

In one aspect of the invention a surgical clamp has an axis extending between a proximal end and a distal end. The clamp includes a support structure together with first and second opposed jaws which are coupled to the support structure. The jaws are disposed at the distal end of the clamp and are operable between an open state, wherein the jaws are spaced to accept a body conduit, and a closed state, wherein the jaws are proximate to occlude the body conduit. The clamp also includes means movable relative to the support structure for engaging at least the second jaw of the clamp to move the second jaw relative to the first jaw between the open state and the closed state.

In another aspect of the invention, a surgical clamp combination includes a clamp having an axis extending between a proximal end and a distal end. The clamp includes a support structure and a pair of jaws disposed at the distal end of the clamp and movable between an open position and a closed position. Moving means is operable from the proximal end of the clamp for moving the jaws between the open position and the closed position. A clamp applier having an axis extending between a proximal end and a distal end includes a tube and engaging means disposed within the tube for engaging the moving means at the proximal end of the clamp. Operating means disposed at the proximal end of the applier functions to rotate the engaging means in the retracted state to move the jaws of the clamp.

In another aspect of the invention, a surgical clamp combination includes a surgical clamp movable between a free state and an operable state. A clamp applier is adapted to releasibly engage the clamp in the free state and to operate the clamp in the operable state to releasibly occlude a body conduit. The applier has a housing disposed at a proximal end and a tube extending toward a distal end and configured to receive the clamp in the operable state. Engaging means is disposed within the tube for engaging the clamp. The combination also includes means for moving the engaging means between an extended position wherein the engaging means can engage the clamp in the free state, and a retracted position wherein the clamp is releasibly held in the operable state.

A method for operating the clamp to occlude a body conduit provides another aspect of the invention. This method includes the step of providing the clamp with a pair of jaws openable to receive the body conduit and closeable to occlude the body conduit. A clamp applier is also provided which has a housing and elongate tube with a distal end extending from the housing and a shaft movable within the tube. By advancing the shaft to an extended position wherein a distal end of the shaft extends beyond the distal end of the tube, the clamp can be engaged with the distal end of the shaft. Retracting the shaft and the clamp to a retracted position and operating the shaft to open the jaws of the clamp enables one to position the clamp over a body conduit. Then, by operating the shaft to close the jaws of the clamp, the body conduit can be occluded.

These and other features and advantages of the invention will be more apparent with a description of preferred embodiments and reference to the associated drawings.

DESCRIPTION OF THE DRAWINGS

FIG. 1 is a perspective view of a clamp being applied by a clamp applier through a trocar to occlude a body conduit;

FIG. 2 is an axial cross-section view of one embodiment of the clamp illustrated in FIG. 1;

FIG. 3 is an axial cross-section view of one embodiment of the clamp applier illustrated in FIG. 1;

FIG. 4 is an axial cross-section view of the applier showing a rotatable shaft deployed to an extended position;

FIG. 5 is a radial cross-section view taken along lines 5—5 of FIG. 3;

FIG. 6 is a perspective view of the clamp aligned for engagement by the rotatable shaft of the clamp applier;

FIG. 7 is an elevation view of the proximal end of the clamp taken along lines 7—7 of FIG. 4;

FIG. 8 is an elevation view of the distal end of the clamp applier taken along lines 8—8 of FIG. 4;

FIG. 9 is a side view, partially in phantom, of the clamp operatively disposed on the clamp applier, and a handle operated to close the clamp;

FIG. 10 is a side view partially in phantom similar to FIG. 9 with the handle operated to open the jaws of the clamp;

DESCRIPTION OF PREFERRED EMBODIMENTS

Figure 11:
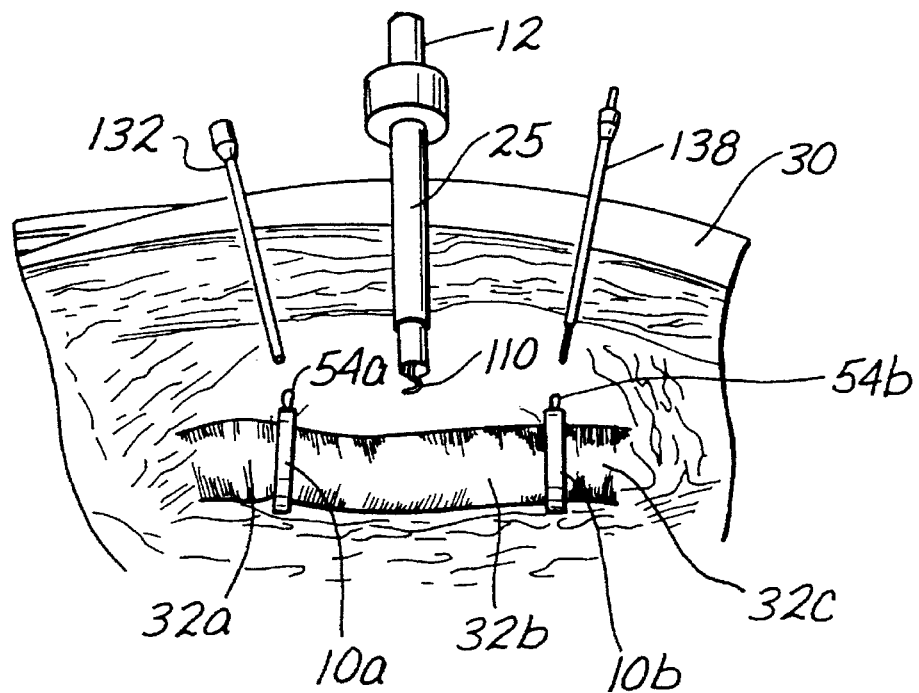
FIG. 11 is a perspective view of the abdominal cavity illustrating the placement of outer clamps in a bowelectomy procedure.

A surgical clamp and clamp applier are illustrated in FIG. 1 and designated respectively by the reference numerals 10 and 12. The clamp 10 has a generally cylindrical configuration with an axis 14 extending between a proximal end 16 and a distal end 18.

The clamp applier 12 includes a housing 21 and a tube 23 which extends distally of the housing 21 along an axis 25. The tube 23 and the clamp 10 are sized and configured to fit through a trocar 27 which has been positioned to provide access across the lapra or abdominal wall 30. Both the trocar 27 and the laparoscopic surgical procedure are described in greater detail in applicant's U.S. Pat. No. 5,209,737 issued on May 11, 1993 and entitled Lever Actuated Septum Seal.

Within the abdominal cavity, the clamp applier can be operated to open and close the clamp 10 about a body conduit, such as a bowel 32. Once the clamp 10 is attached to the bowel 32 it can function not only to occlude but also to cooperate with a retractor to move the bowel to a new location within the abdominal cavity.

In FIG. 2, the clamp 10 is illustrated in an axial cross-section view to include a supporting structure 34 and a pair of jaws 36 and 38. In the illustrated embodiment, the jaw 36 is formed as an extension of the supporting structure 34, while the jaw 38 is pivotal on the jaw 36 at a hinge 41.

The jaws 36 and 38 extend longitudinally toward the distal end 18 of the clamp 10 where one of the jaws, such as the jaw 38 is provided with an overhang 43. As the jaw 38 moves into proximity with the jaw 36, the overhang 43 encloses the bowel 32 prior to complete occlusion. This insures that the bowel 32 is captured between the jaws 36, 38 as the final occluding pressure is applied.

At the proximal end of the jaw 38, distally of the supporting structure 34, the jaw 38 is provided with a beveled surface 45 which faces inwardly toward the axis 14 of the clamp 10. This surface 45 functions in a camming action with a screw 47 which is rotatable within the supporting structure 34. In the preferred embodiment, the screw 47 is disposed for movement along the axis 14 of the clamp 10. As the screw 47 is rotated it moves axially through the supporting structure 34 to engage the beveled surface 45. Further axial movement of the screw 47 forces the jaw 38 to pivot on the hinge 41. This pivotal movement moves the jaw 38 from an open state illustrated in FIG. 2, wherein the jaw 38 is spaced from the jaw 36, to a closed state illustrated in FIG. 1 wherein the jaw 38 is brought into proximity with the jaw 36. In the closed state, the body conduit, such as the bowel 32, which is disposed between the jaws 36 and 38, is at least partially occluded. Soft inserts 49 can be provided along the jaws 36 and 38 to reduce trauma to the bowel 32.

A spring 52 can be provided in the hinge 41 in order to bias the jaws 36 and 38 to the open position. When the screw 47 is retracted, the jaw 38 will automatically separate from the jaw 36. When the screw 47 is advanced, the jaw 38 moves toward the jaw 36 against the bias of the spring 52. In an alternative embodiment (not shown), both of the jaws 36 and 38 are pivotal along the supporting structure 34 and include bevel surfaces, such as surface 45, which are engagable by the screw 47 to open and close the jaws 36, 38.

At the proximal end of the screw 47, an annulus 54 can be provided in order to facilitate attachment to the clamp applier 12. The annulus 54 preferably has an axis 55 which perpendicularly intersects the axis 14 of the clamp 10.

The clamp applier 12 is illustrated in the axial cross-section view of FIG. 3 which shows the interior regions of the housing 21 and the tube 23. The tube 23 is attached to the distal end of the housing 21 where a distal wall 56 extends generally perpendicular to the axis 25.

A shaft 58 extends through the tube 23 and proximally through a hole 61 in the distal wall 56 into the housing 21. Within the housing 21, the shaft 58 extends through a wafer 62 and terminates in the distal end of an aladdin screw 63. At its proximal end, the diameter of the aladdin screw 63 is decreased to define a proximal facing shoulder 65, increased to define a distally facing shoulder 67, and enlarged again at a distally facing shoulder 69 formed on a terminal lug 70. The aladdin screw 63 has an outer cylindrical surface which is provided with counter-rotating spiral grooves 72 and 74.

A trigger 81 pivotal on the housing 21 operates a pair of fingers 83 and 85. These fingers are closely spaced to receive the reduced diameter of the aladdin screw 63 between the shoulders 65 and 67. A handle 90 fixed to the housing 21 provides support, in the palm of a user's hand (not shown), against which the trigger 81 can be operated. Pulling the trigger causes the fingers 83, 85 to engage the proximally facing shoulder 65 and to move the aladdin screw 63 and associated shaft 58 distally as illustrated in FIG. 4.

With the wafer 62 fixed to the shaft 58 and the wall 56 fixed to the housing 21, a compression spring 92 disposed therebetween around the shaft 58 functions to bias the aladdin screw 63 and shaft 58 toward a proximal retracted position. This proximal position is illustrated in FIG. 3 along with a locking mechanism which functions to maintain the screw 63 and the shaft 58 in the proximal position. The locking mechanism includes a second trigger 96 and a pair of fingers 98 and 101 which engage the aladdin screw between the shoulders 67 and 69. In a preferred embodiment, these fingers 98, 101 extend perpendicular to the axis 25 and abut the distally facing shoulder 69 to hold the terminal lug 70 in a locked proximal position. When the trigger 96 is in a distal position, spaced from the handle 90, the aladdin screw 63 and shaft 58 are locked in the proximal position. When the trigger 96 is pulled against the handle 90 as illustrated in FIG. 4, the fingers 98 and 101 are removed from the terminal lug 70 to permit distal movement of the screw 63 and shaft 58. When both of the triggers 81 and 96 are moved against the handle 90, the trigger 96 initially releases the lock as the trigger 81 deploys the screw 93 and shaft 58 to the distal extended position.

The proximal and distal positions of the shaft 58 are best described with reference to the distal end of the shaft 58 which is formed in the shape of a hook 110. In a preferred embodiment, the distal end of the hook 110 includes a terminal portion 112 which extends generally perpendicular to the axis 25. The hook 110 is sized and configured to engage the annulus 54 at the proximal end of the clamp 10. Thus the hook 110 and shaft 58 function as an engagement mechanism for initially engaging the clamp 10 and ultimately moving the clamp into operative disposition relative to the tube 23.

The trigger 81 functions to deploy this engaging mechanism to the distal position wherein the hook 110 extends beyond the end of the tube 23. In this position the terminal end 112 of the hook 110 is accessible for insertion into the annulus 54. In FIG. 6, the clamp 10 is illustrated in a free state wherein it is not attached to the clamp applier 12. Once the hook 110 engages the annulus 54 and the trigger 81 is released, however, the spring 92 functions to move the shaft 58 and hook 110 to the proximal position drawing the annulus 54 of the clamp 10 into the tube 23. In a preferred embodiment, this brings the clamp 10 into abutting relationship with the distal end of the tube 23 wherein the axes 14 and 25 are aligned to facilitate insertion through the trocar 27.

It will be apparent that the clamp 10 can be otherwise engaged by the shaft 58 of the applier 12 in a locking but operative position. In general, the screw 47 needs to be positively engaged by the shaft 58 so that the clamp 10 cannot be accidentally dropped into the abdominal cavity. This positive engagement between the clamp 10 and shaft 58 must also be capable of transmitting the rotational movement of the shaft 58 to the screw 47.

In this operative position, the supporting structure 34 of the clamp 10 can be held against axial movement by the locking mechanism including the trigger 96. The supporting structure of the clamp 10 is held against rotational movement relative to the tube 23 by a key 114 on the supporting structure 34 and associated key way 116 on the tube 23. In a preferred embodiment, the key 114 is formed with four sides which are equally spaced around and inclined proximally toward the axis 14. This key 114 registers with similar surfaces which are formed on the inside of the tube 23 and define the key way 116. At the base of the key 114, the supporting structure 34 forms a proximally facing shoulder 118, best illustrated in FIG. 2. This shoulder 118 is adapted to register with a distal surface 121 on the tube 23. Other configurations for the key 114 and key way 116 will be apparent. In general, it is desirable that the key 114 can be tapered inwardly, proximally in order to achieve axial alignment of the clamp 10 and tube 23. Any noncircular shape for the key 114 and key way 116 would appear to inhibit rotational movement between the clamp 10 and tube 23.

When the clamp 10 is operatively disposed, the annulus 54 is engaged by the hook 110 interiorly of the tube 23. The key 114 registers with the key way 116, and the shoulder 118 is in abutting relationship with the surface 121. With the proximal bias on the shaft 58, the clamp 10 is automatically moved to this operative position where it can be locked in place by operation of the trigger 96.

Once the clamp 10 is operatively disposed at the distal end of the clamp applier 12, it will normally be desirable to operate the screw 47 in order to open and close the jaw 38. This rotation of the screw 47 is accomplished in a preferred embodiment by rotating the shaft 58. For exampled as illustrated in FIG. 3, a second handle 130 can be provided on the housing 21 for engagement by the fingers of a user's hand. This handle is fixed to a follower block 132 which is movable along the housing 21 in cooperation with the aladdin screw 63. This follower block 132 includes a follower 133 movable between two positions by operation of a tab 134 which is accessible outside the housing 21.

In accordance with the normal operation of an aladdin screw, the tab 134 is operable to bring the follower 133 into registration with one of the grooves 72 and 74. When the follower 133 engages the groove 74 for example, movement of the handle 130 toward the handle 90 causes the aladdin screw 63 to rotate in a clockwise direction. This causes the shaft 58 to rotate in a clockwise direction and to advance the screw 47 of the clamp 10 toward the beveled surface 45. When the tab 134 is operated to move the follower into engagement with the groove 72, movement of the handle 130 toward the handle 90 rotates the aladdin screw 63 in a counterclockwise direction. This causes the shaft 58 to move counterclockwise and the screw 47 to be withdrawn from the beveled surface 45 permitting to jaws 36, 38 the open.

Thus the aladdin screw and associated follower 133, tab 34 and handle 130 function so that the linear movement of the handle 130 is converted into rotational movement of the shaft 58. In this particular embodiment, movement of the handle 130 in a single direction, toward the handle 90, can produce either clockwise or counter-clockwise rotation of the shaft 58 depending on the position of the tab 134 and associated follower 133.

In a preferred method associated with the invention, the clamp 10 is initially in a free state, unattached to the clamp applier 12. In order to prepare the applier 12 to receive the clamp 10, the shaft 58 initially must be unlocked. This requires that the trigger 96 be pulled against the handle 20 in order to remove the fingers 98, 101 from the shoulder 69 of the terminal lug 70. Thus operation of the trigger 96 elevates the fingers 98, 101 as illustrated in FIG. 4, to free the shaft 58 for axial movement along the axis 25.

In this unlocked state, the shaft 58 is biased in the retracted position so that operation of the trigger 81 is required to deploy the hook 110. By pulling the trigger 81 against the handle 90, the fingers 83, 85 are brought into engagement with the shoulder 65. Further proximal movement of the trigger 81 moves the aladdin screw 63 and shaft 58 against the bias of the spring 92 to the extended position illustrated in FIG. 4.

In this extended position, the terminal end 112 of the hook 110 can be introduced through the annulus 54 to engage the clamp 10. When the trigger 81 is released, the bias of the spring 92 moves the shaft and aladdin screw 63 toward the retracted position. The hook 110 is drawn into the tube 23 along with the annulus 54, and the key 114 on the clamp 10 registers with the key way 116 at the distal end of the tube 23. When the shoulders 118 abut the distal surface 121, the clamp 10 has achieved its operative position. It can be retained in this position by moving the trigger 96 distally so that the fingers 98, 101, engage the shoulder 69 on the terminal lug 70.

In this operative position, registration of the key 114 and key way 116 seeks to align the axis 14 of the clamp 10 with the axis 25 of the clamp applier 12. Axial movement of the clamp 10 relative to the applier 12 is inhibited by the locking mechanism, while rotational movement of the clamp 10 relative to the applier 12 is inhibited by the registration of the key 114 and key way 116. In this operative position, the shaft 56 can be rotated in two directions to either open or close the jaws 36, 38.

In an embodiment including the aladdin screw 63, operation of the handle 130 in a single direction, for example toward the handle 90, can cause rotation of the shaft 58 in either of the two directions. For example, if the tab 134 is positioned so that the follower 133 engages the groove 74, movement of the handle 130 toward the handle 90 will be converted into clockwise rotation of the shaft 58. This will cause the screw 47 to advance into the beveled surface 45 causing the jaws 36 and 38 as illustrated in FIG. 9. Alternatively, with the tab 134 disposed in the opposite position, the follower 133 engages the groove 72 of the aladdin screw 63. Then, movement of the handle 130 toward the handle 90 can be converted into rotational movement of the shaft 58 in the counter-clockwise direction. This will remove the screw 47 from the beveled surface 45 resulting in separation of the jaws 36, 38 by operation of the spring 52, as illustrated in FIG. 10.

While the aladdin screw 63 is incorporated in a preferred embodiment, it will be apparent that a single screw could also be used. In such an embodiment, operation of the handle 130 toward the handle 90 could result in the clockwise rotation of the shaft 58 while movement of the handle 130 away from the handle 90 would result in counter-clockwise rotation of the shaft 58.

The foregoing apparatus and method are of particular interest in a surgical procedure providing for removal of a section of the bowel 32. This procedure is illustrated in FIG. 11–14 wherein three sections of the bowel are designated consecutively by the reference numerals 32a, 32b and 32c. In this procedure, it is the center section 32b which is to be removed.

Initially a clamp 10a is engaged by the clamp applier 12 and inserted through the trocar 25 to operatively occlude the bowel between the section 32a and 32b. After the clamp 10a has been operatively positioned, the applier 12 can be operated to disengage the hook 110 from the associated annulus 54a. Then a second clamp 10b is operatively disposed to occlude the bowel between the section 32b and the section 32c. After the clamp 10b has been positioned, the clamp applier 12 can be operated to release the hook 110 from the associated annulus 54b.

Figure 12:
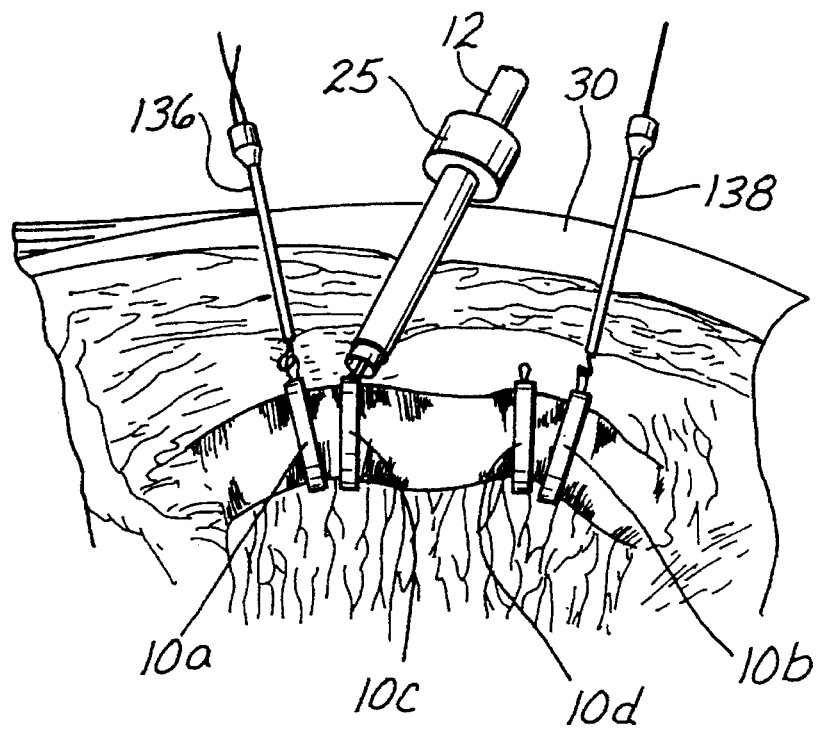
FIG. 12 is a perspective view similar to FIG. 11 showing the placement of inner clamps in the procedure.

At this point it may be desirable to elevate the bowel 32 in order to provide better access within the abdominal cavity. For this purpose, retractors 136 and 138 can be introduced through the abdominal wall 30 to engage the respective annulus 54a and 54b. Alternatively, the retractors 136, 138 can be introduced through secondary trocars (not shown) similar to the trocar 25. Once the clamps 10a and 10b have been engaged by the respective retractors 136,138, they can be moved toward the abdominal wall 30 to elevate the bowel 32 as illustrated in FIG. 12.

In this elevated location, two additional clamps 10c and 10d can be attached to occlude the bowel 32 adjacent the respective clamps 10a and 10b. These clamps 10c and 10d can also be released and the clamp applier 12 removed from the trocar 25.

Figure 13:
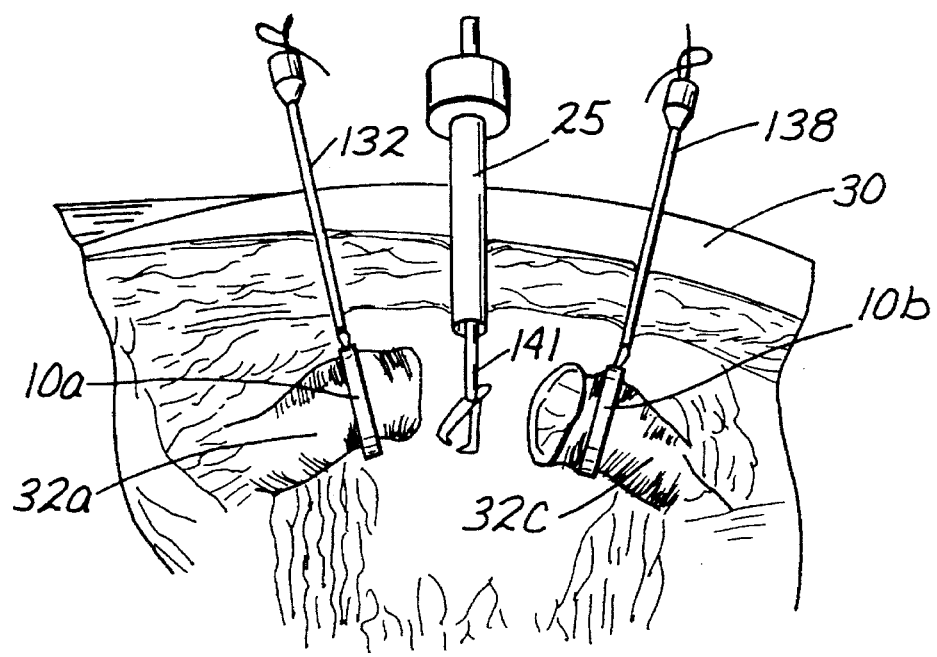
FIG. 13 is a perspective view similar to FIG. 11 illustrating the removal of a bowel section from the abdominal cavity.
Figure 14:
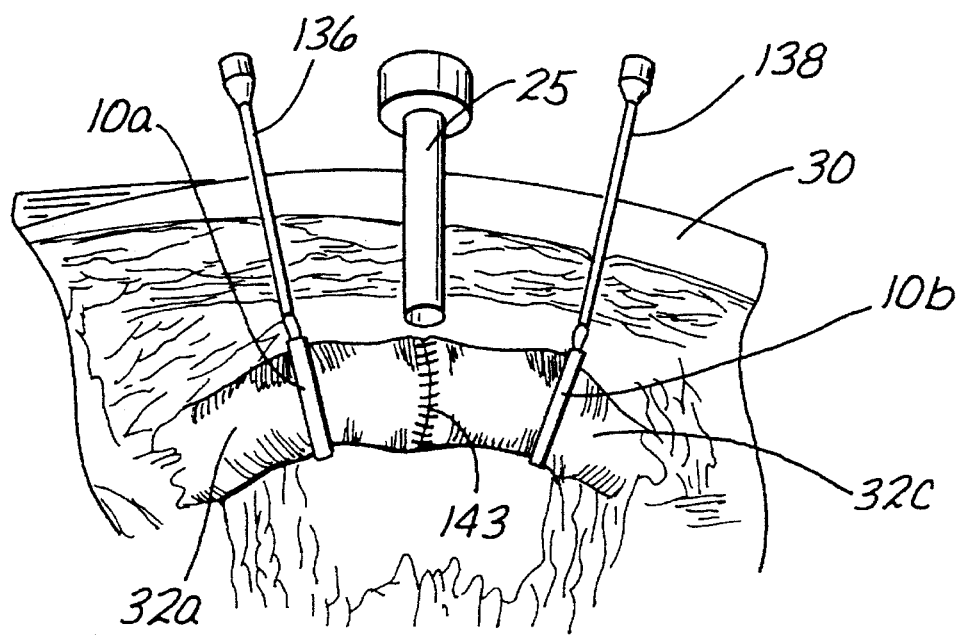
FIG. 14 is a perspective view similar to FIG. 11 illustrating the suturing of the bowel following removal of the bowel section.

With the clamps 10a–10d appropriately positioned, the center section 32b of the bowel 32 can be severed from the sections 32a and 32c by appropriate incisions between the clamp pairs 10a, 10c and 10d, 10b. At this point, the clamp applier 12 can be reinserted through the trocar 25 to engage the clamps 10c and 10d and to remove these clamps through the trocar 25. A grasper 141 may also be inserted to withdraw the central section 32b of the bowel, as illustrated in FIG. 13. Finally, a suturing mechanism (not shown) can be introduced through the trocar 12 to facilitate the placement of sutures 143 between the bowel portion 32a to the bowel portion 32c.

At the completion of this step, the retractors 136, 138 can be operated to disengage the clamps 10a, 10b, and the clamp applier 12 can be reintroduced to retrieve the clamps 10a, 10b. Ultimately the retractors 136, 138 and the trocar 25 are removed from the abdominal wall 30 to complete the procedure.

In the foregoing discussion, a preferred embodiment, clamp applier, and associated methods have been described. Many variations on this concept will now be apparent. For example, many clamp configurations can be adapted to provide a generally cylindrical configuration with jaws openable and closeable by operation of a mechanism generally along the axis of the clamp. With these constraints, the clamp can be introduced through a trocar to facilitate a wide variation in laparoscopic procedures.

Both apparatus and methods for operating such a clamp with an appropriate clamp applier will also be apparent. Initially the applier must have an elongate configuration also sized and configured to fit through a trocar. A appropriate mechanism for holding the clamp in a fixed operable position will be desirable. Once the clamp is in this position, an appropriate mechanism will open and close the jaws of the clamp.

Given the wide variation in the possibilities for embodying this concept, one is cautioned not to determine the scope of the invention merely with reference to the drawings and associated description, but rather with reference to the following claims.

What is claimed is:

1. A surgical clamp having a longitudinal configuration and an axis extending between a proximal end and a distal end of said clamp, the clamp comprising:

a support structure;

first and second opposed jaws coupled to the support structure, the first jaw being pivotally attached to one of the support structure and the second jaw and the jaws being operable between an open state wherein the first jaw is spaced from the second jaw to accept a body conduit, and a closed state wherein the jaws are proximate to at least partially occlude the body conduit;

means carried by the clamp for biasing the first jaw to the open state;

a portion of the first jaw defining a beveled surface which is disposed at an angle to the axis of the clamp;

means carried by the support structure and movable relative to the support structure for engaging at least the first jaw to move the first jaw relative to the second jaw between the open state and the closed state; and a screw included in the engaging means and disposed at the proximate end of the clamp, the screw being operable to move axially along the beveled surface of the first jaw in the open state to move the first jaw toward the closed state.

2. The surgical clamp recited in claim 1 wherein the screw further comprises an annulus disposed at the proximal end of the clamp, the annulus being externally engagable to rotate the screw and to move the screw along the axis of the clamp.

3. A surgical clamp combination, comprising:

a surgical clamp having a longitudinal axis extending between a proximal end and a distal end, and including a supporting structure;

a pair of jaws coupled to the supporting structure, the jaws being movable between an open position and a closed position;

moving means carried by the supporting structure and operable from the proximal end of the clamp for moving the jaws between the open position and the closed position and comprising a screw rotatable along the axis of the clamp to operatively engage at least one of the jaws of the clamp;

a clamp applier having a longitudinal axis extending between a proximal end and a distal end;

a tube disposed at the distal end of the clamp applier;

engaging means disposed within the tube for engaging the moving means at the proximal end of the clamp; and operating means disposed at the proximal end of the applier for operating the engaging means to move the jaws of the clamp.

4. The combination recited in claim 3 wherein the clamp applier comprises:

a housing;

means for coupling the tube to the housing; a handle coupled to said housing and movable relative to the housing; and means for converting the movement of the handle into rotational movement of the engaging means.

5. The combination recited in claim 4 wherein the handle is movable generally linearly of the housing and the converting means includes means for converting the linear movement of the handle into rotational movement of the engaging means.

6. The combination recited in claim 3 further comprising:

means defining a key at the proximal end of the clamp;

means defining a key way at the distal end of the clamp applier; wherein the key of the clamp is removably registerable with the key way of the applier to prevent rotational movement of the supporting structure of the clamp relative to the tube of the applier while permitting rotational movement of the screw of the clamp and the engaging means of the applier.

7. The combination recited in claim 6 wherein the key of the clamp is registered with the key way of the applier when the axis of the clamp is aligned with the axis of the applier.

8. The combination recited in claim 6 further comprising:

a first coupler fixed to the screw at the proximal end of the clamp;

a second coupler included in the engaging means at the distal end of the clamp applier;

the first and second couplers being configured for operative engagement whereby rotation of the engaging means rotates the screw to operate the jaws of the clamp.

9. A surgical clamp combination comprising:

a surgical clamp movable between a free state and an operable state;

a clamp applier adapted to releasably engage the clamp in the free state and to operate the clamp in the operable state to releasably occlude a body conduit, the applier having an axis extending between a proximal end and a distal end;

a housing disposed at the proximal end of the applier;

a tube extending distally of the housing and configured to receive the clamp in the operable state;

engaging means disposed within the tube for engaging the clamp, the engaging means including a rotatable shaft and means disposed at the distal end of the applier for coupling the shaft to the clamp;

means connected to the engaging means for moving the engaging means between an extended position wherein the engaging means can engage the clamp in the free state, and a retracted position wherein the clamp is releasably held in the operable state; and means connected to the applier for rotating the shaft of the applier to operate the clamp in the operable state.

10. The combination recited in claim 9 wherein the moving means comprises:

means for biasing the engaging means to the retracted position; and means for advancing the engaging means against the bias of the biasing means toward the extended position.

11. The combination recited in claim 10 wherein the moving means includes a trigger pivotal on the housing of the clamp applier and operable to move the engaging means axially to the extended position.

12. The combination recited in claim 10 further comprising:

means disposed in said housing for locking the engaging means in the retracted position.

13. The combination recited in claim 12 wherein the locking means comprises a trigger pivotal on the housing to prevent axial movement of the engaging means.

14. The combination recited in claim 9 further comprising:

a handle included in the rotating means and moveable along the housing; and means for converting movement of the handle into rotational movement of the shaft.

15. A surgical clamp combination comprising:

a surgical clamp movable between a free state and an operable state;

a clamp applier adapted to releasably engage the clamp in the free state and to operate the clamp in the operable state to releasably occlude a body conduit, the applier having an axis extending between a proximal end and a distal end;

a housing disposed at the proximal end of the applier;

a tube extending distally of the housing and configured to receive the clamp in the operable state;

engaging means disposed within the tube for engaging the clamp;

means for moving the engaging means between an extended position wherein the engaging means can engage the clamp in the free state, and a retracted position wherein the clamp is releasably held in the operable state, comprising a means for biasing the engaging means to the retracted position, and means for advancing the engaging means against the bias of the biasing means toward the extended position; and means disposed in the housing for locking the engaging means in the retracted position.

16. A surgical clamp combination, comprising:

a surgical clamp having a longitudinal axis extending between a proximal end and a distal end, and including a supporting structure;

a pair of jaws coupled to the supporting structure, the jaws being movable between an open position and a closed position;

moving means disposed on the clamp and operable from the proximal end of the clamp for moving the jaws between the open position and the closed position;

a clamp applier having a longitudinal axis extending between a proximal end and a distal end;

a tube disposed at the distal end of the clamp applier;

engaging means disposed within the tube for engaging the moving means at the proximal end of the clamp; and operating means disposed at the proximal end of the applier for operating the engaging means to move the jaws of the clamp;

wherein the clamp applier does not include any cradle structure for carrying and supporting said surgical clamp.

17. The combination recited in claim 16 wherein the moving means comprises:

a screw rotatable along the axis of the clamp to operatively engage at least one of the jaws of the clamp.

18. The combination recited in claim 17 wherein the clamp applier comprises:

a housing;

means for coupling the tube to the housing;

a handle movable relative to the housing; and means connected to the handle for converting the movement of the handle into rotational movement of the engaging means.

19. The combination recited in claim 18 wherein the handle is movable generally linearly of the housing and the converting means includes means for converting the linear movement of the handle into rotational movement of the engaging means.

20. The combination recited in claim 17 and further comprising:

means defining a key at the proximal end of the clamp;

means defining a key way at the distal end of the clamp applier; wherein the key of the clamp is removably registerable with the key way of the applier to prevent rotational movement of the supporting structure of the clamp relative to the tube of the applier while permitting rotational movement of the screw of the clamp and the engaging means of the applier.

21. The combination recited in claim 20 wherein the key of the clamp is registered with the key way of the applier when the axis of the clamp is aligned with the axis of the applier.

22. The combination recited in claim 17 and further comprising:

a first coupler fixed to the screw at the proximal end of the clamp;

a second coupler included in the engaging means at the distal end of the clamp applier;

the first and second couplers being configured for operative engagement whereby rotation of the engaging means rotates the screw to operate the jaws of the clamp.

* * * * *

UNITED STATES PATENT AND TRADEMARK OFFICE
CERTIFICATE OF CORRECTION

PATENT NO. : 5,496,333
DATED : March 5, 1996
INVENTOR(S) : Sackier et al.

It is certified that error appears in the above-identified patent and that said Letters Patent is hereby corrected as shown below:

<u>Title page,</u>
Under the subsection of Inventors 75 ; after "Edward E. Dolendo, Huntington Beach," please insert -- Charles C. Hart, Huntington Beach, --.

Signed and Sealed this

Second Day of October, 2001

*Attest:*

*Attesting Officer*

NICHOLAS P. GODICI
*Acting Director of the United States Patent and Trademark Office*